United States Patent [19]

Giannessi et al.

[11] Patent Number: 5,714,619
[45] Date of Patent: Feb. 3, 1998

[54] PROCESS FOR THE PREPARATION OF (S)-β-HYDROXY-γ-BUTYROLACTONE

[75] Inventors: Fabio Giannessi; Francesco De Angelis, both of Rome, Italy

[73] Assignee: Sigma-Tau Industrie Farmaceutiche Riunite S.p.A., Rome, Italy

[21] Appl. No.: 678,684

[22] Filed: Jul. 11, 1996

[30] Foreign Application Priority Data

Sep. 29, 1995 [IT] Italy .................. RM95A0652

[51] Int. Cl.[6] .................. C07D 307/33
[52] U.S. Cl. .................. 549/313
[58] Field of Search .................. 549/313

[56] References Cited

U.S. PATENT DOCUMENTS 5,412,113  5/1995  Giannessi et al. .......... 549/328
5,491,260  2/1996  Giannessi et al. .......... 549/328
5,532,409  7/1996  Giannessi et al. .......... 562/561
5,532,410  7/1996  Giannessi et al. .......... 562/567

OTHER PUBLICATIONS

Lowes et al., Analyst, vol. 115, pp. 511–516 (May 1990).

*Primary Examiner*—Bernard Dentz
*Attorney, Agent, or Firm*—Oblon, Spivak, McClelland, Maier & Neustadt, P.C.

[57] ABSTRACT

A process for producing (S)-β-hydroxy-γ-butyrolactone, a versatile intermediate used in several organic syntheses, from (S)-carnitine which is an unexpensive waste-product obtained from the production of (R)-carnitine by the resolution of racemic mixtures, is disclosed.

6 Claims, No Drawings

PROCESS FOR THE PREPARATION OF (S)-β-HYDROXY-γ-BUTYROLACTONE

The present invention relates to a process for preparing (S)-β-hydroxy-γ-butyrolactone.

(S)-β-hydroxy-γ-butyrolactone having the formula:

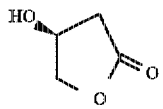

is a versatile chiral intermediate. In fact, it is used in several industrial synthesis such as:
(1) the preparation of S-oxiracetam
   PCT WO 9306826 (Smith-Kline Beecham)
   C.A.: 119, 139083 y 1993;
(2) the preparation of esters of 5,6-hydroxy-3-keto-hexanoic acid
   J.P. 04173767
   C.A.: 118, 21945 g. 1193 (Kanegafuchi);
(3) the synthesis of natural substances e.g. multistriatine
   Tetrahedron 43/10, 2303, (1987)
   C.A.: 108, 94236 e.

The known methods for synthesizing (S)-β-hydroxy-γ-butyrolactone entail several steps and achieve low yields.

The synthesis starting from the unexpensive ascorbic acid provides low yields of the R form only.

Even though the synthesis (described in Chemistry Letters, 1389–1392, 1984) from dimethyl-S-malate (a valuable product available on the market), provides the product in two steps with an overall 80% yield, it entails the utilization of reagents such as the borane-dimethylsulfide complex, sodium borohydride and trifluoroacetic acid. These reagents present considerable drawbacks when utilized in processes conducted on an industrial-scale.

Finally, the 3-step synthesis disclosed in JP 04,266,881 (yield 66%) requires an asymmetric epoxydation with Ti(OCHMe$_2$)$_4$ and diisopropyl-D-tartrate, a catalytic hydrogenation with Pd/C and an ozonolysis. These reactions are hardly applicable on an industrial-scale. Moreover, the starting product is not easily available on the market.

On the contrary, the process of this invention offers remarkable advantages over the known synthesis of (S)-β-hydroxy-γ-butyrolactone.

One of these advantages consist in using (S)-carnitine as starting compound which is an economical waste-product obtained during the preparation of (R)-carnitine (of which are known several therapeutic uses) in equimolar amount with respect to (R)-carnitine. In fact the processes used to date for the preparation of (R)-carnitine are based on the resolution of racemic mixtures.

As known, carnitine contains a single centre of asymmetry and therefore exists as two enantiomers, designated (S)-carnitine and (R)-carnitine, respectively. Of these, only R-carnitine is found in living organisms, where it functions as a vehicle for transporting fatty acids across mitochondrial membranes. Whilst (R)-carnitine is the physiologically-active enantiomer, for some years racemic R,S-carnitine had been used as a therapeutic agent. It is now recognized, however, that (S)-carnitine is a competitive inhibitor of carnitine acyltransferases, and that it can diminish the level of (R)-carnitine in myocardium and skeletal muscle.

It is, therefore, essential that only (R)-carnitine be administered to patients undergoing haemodialysis treatment or treatment for cardiac or lipid metabolism disorders. The same requirement applies to the therapeutic utilization of acyl derivatives of carnitine.

Various chemical processes have been proposed for the industrial-scale production of (R)-carnitine. These processes are not stereospecific, leading to racemic R, S mixtures. Consequently, it becomes necessary to apply methods of resolution in order to separate the enantiomeric constituents of the racemate. Tipically, the R,S racemic mixture is reacted with an optically active acid, selected e.g. from S-(−)-tartaric acid, S-(+)-camphorsulfonic acid, (+)-dibenzoyl S(−)-tartaric acid, N-acetyl-R(+)-glutamic acid and (S)-(+)-camphoric acid, thus obtaining two diastereoisomers which can be separated from each other. In the classic process disclosed in U.S. Pat. No. 4,254,053, (S)-(+)-camphoric acid is used as resolution agent of a racemic mixture of R,S-carnitinamide, obtaining (S)-(+)-carnitinamide as by-product, and (R)-(−)-carnitinamide which is hydrolyzed to R(−)-carnitine. Also (S)-(+)-carnitinamide can be easily converted to (S)-(+)-carnitine.

In the last years, the utilization of such cumbersome waste-product has been the target of various research programs, and the process of this invention offers a solution for such problem.

Furthermore, by the process of this invention (S)-β-hydroxy-γ-butyrolactone is obtained in a single step with high yields.

The object of the present invention is to provide a process for preparing (S)-β-hydroxy-γ-butyrolactone (I) by direct conversion of (S)-carnitine to (I) according to the following reaction scheme:

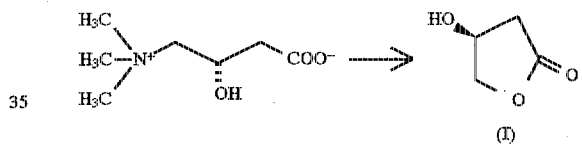

which comprises:
preparing a solution of (S)-carnitine inner salt in a solvent, inert to the conversion, keeping the solution thus obtained at 100°–190° C., for 0.5–5 hours, and
isolating (I) by solvent evaporation.

Instead of (S)-carnitine inner salt, any (S)-carnitine salt can be used. In this case, its solution in the inert solvent shall contain an equimolar mount of a base such as e.g. NaHCO$_3$, NaOH or Et$_3$N.

The solvent is an aprotic dipolar solvent selected from DMSO and DMF.

Alternatively, the solvent is a mixture of CH$_3$CN/H$_2$O (ratio 100/0.1 to 100/10) and the resulting solution is kept at a temperature from 80° C. to the reflux temperature of the solution, for 1–7 days.

The following example illustrates the invention without limiting it.

PREPARATION OF (S)-β-HYDROXY-γ-BUTYROLACTONE

A solution of S-carnitine inner salt (5 g; 0.031 moles) in 100 ml of DMSO was kept under stirring at 150° C. for one hour.

The solvent was evaporated under vacuum and the residue was purified by chromatography on silica gel using EtOAc as eluant. Following solvent evaporation, 2.6 g of an oily product were obtained.

Yield: 82%

$[\alpha]_D^{20} = -88.2°$ (c=0.8; MeOH)

TLC=silica gel eluant=EtOAc Rf: 0.64
Elementary analysis for $C_4H_6O_3$
Calculated C=47.06% H=5.92%
Found C=46.84% H=5.76%
$^1HNMR(CDCl_3)$=δ4.65(m, 1H, —C$\underline{H}$OH), 4.4(dd, 1H, —C$\underline{H}$HOCO—, J=10.5 Hz, J=4.5 Hz); 4.28(dm, 1H, —CH$\underline{H}$OCO—, J=10.5 Hz); 3.5(br, 1H, OH), 2.72(dd, 1H, —C$\underline{H}$HCOO—, J=5.5 Hz, J=18 Hz), 2.5(dm, 1H, —CH$\underline{H}$COO—, J=18 Hz)

HPLC
Column=µBondapack —C18 (10 µm) diameter=3.9 mm
length=300 mm
Eluant=$KH_2PO_4$ 50 mM (100%)
Flow rate=1.0 ml/min
Retention time=4.22 min
Detector=U.V. 205 nm waters 481

We claim:

1. A process for preparing (S)-β-hydroxy-γ-butyrolactone (I) by direct conversion of (S)-carnitine inner salt to (I) according to the following reaction scheme:

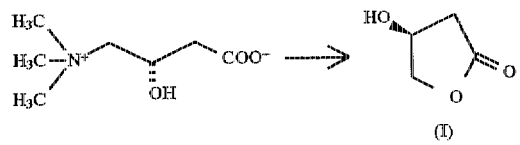

which comprises:
preparing a solution of (S)-carnitine inner salt in a solvent inert to the conversion, keeping the solution thus obtained at 100°–190° C. for 0.5–5 hours, and
isolating (I) by solvent evaporation.

2. A process for preparing (S)-β-hydroxy-γ-butyrolactone (I) by direct conversion of an (S)-carnitine salt to (I) according to the following reaction scheme:

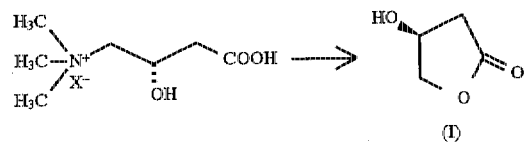

wherein X⁻ is an anion which comprises:
preparing a solution of the (S)-carnitine salt and an equimolar amount of a base in a solvent inert to the conversion, keeping the solution thus obtained at 100°–190° C., for 0.5–5 hours, and
isolating (I) by solvent evaporation.

3. The process of claim 2, wherein the base is selected from $NaHCO_3$, NaOH and $Et_3N$.

4. The process of claim 1 or 2, wherein the solvent is an aprotic dipolar solvent selected from DMSO and DMF.

5. A process for preparing (S)-β-hydroxy-γ-butyrolactone (I) by direct conversion of (S)-carnitine inner salt of (I) according to the following reaction scheme:

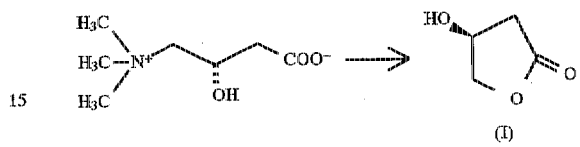

which comprises:
preparing a solution of (S)-carnitine inner salt in a solvent inert to the conversion,
wherein the solvent is a $CH_3CN/H_2O$ mixture, and the resulting solution is kept at a temperature from 80° C. to the reflux temperature of the solution, for 1–7 days, and isolating (I) by evaporation.

6. A process for preparing (S)-β-hydroxy-γ-butyrolactone (I) by direct conversion of an (S)-carnitine salt to (I) according to the following reaction scheme:

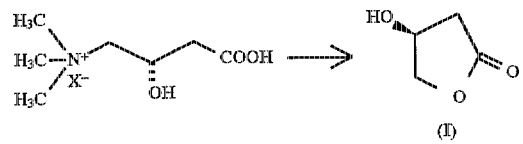

wherein X is any anion which comprises:
preparing a solution of the (S)-carnitine salt and an equimolar amount of a base in a solvent inert to the conversion,
wherein the solvent is a $CH_3CN/H_2O$ mixture, and the resulting solution is kept at a temperature from 80° C. to the reflux temperature of the solution, for 1–7 days, and isolating (I) by evaporation.

* * * * *

UNITED STATES PATENT AND TRADEMARK OFFICE
CERTIFICATE OF CORRECTION

PATENT NO. : 5,714,619
DATED : FEBRUARY 3, 1998
INVENTOR(S) : FABIO GIANNESSI ET AL

It is certified that error appears in the above-identified patent and that said Letters Patent is hereby corrected as shown below:

Column 2, line 8, "Tipically" should read --Typically--.

Column 3, line 1, "Rf: 0.64" should read --Rf=0.64--.

Signed and Sealed this

Twenty-second Day of September, 1998

Attest:

BRUCE LEHMAN

*Attesting Officer*           *Commissioner of Patents and Trademarks*